(12) United States Patent
Sproul

(10) Patent No.: US 6,582,439 B1
(45) Date of Patent: Jun. 24, 2003

(54) VERTEBROPLASTY SYSTEM

(75) Inventor: Michael E. Sproul, Tequesta, FL (US)

(73) Assignee: Yacmur LLC, Jupiter, FL (US)

( * ) Notice: Subject to any disclaimer, the term of this patent is extended or adjusted under 35 U.S.C. 154(b) by 0 days.

(21) Appl. No.: 10/035,670

(22) Filed: Dec. 28, 2001

(51) Int. Cl.⁷ .......................... A61B 17/58; A61B 17/56
(52) U.S. Cl. ............................................ 606/92; 606/86
(58) Field of Search ............................ 606/92, 86, 167, 606/93, 94, 99, 61; 604/264, 272, 273, 274, 158, 170.01, 170.02, 170.03, 164.01, 164.09, 38, 95.03; 623/8, 66; 600/566, 567

(56) References Cited

U.S. PATENT DOCUMENTS

| | | |
|---|---|---|
| 4,369,772 A | 1/1983 | Miller |
| 4,576,152 A | 3/1986 | Muller et al. |
| 5,052,243 A | 10/1991 | Tepic |
| 5,431,654 A | 7/1995 | Nic |
| 5,634,473 A | 6/1997 | Goldenberg et al. |
| 5,843,001 A | 12/1998 | Goldenberg |
| 6,019,776 A | 2/2000 | Preissman et al. |
| 6,048,346 A | 4/2000 | Reiley et al. |
| 6,214,012 B1 | 4/2001 | Karpman et al. |
| 6,241,734 B1 | 6/2001 | Scribner et al. |
| 6,248,110 B1 | 6/2001 | Reiley et al. |
| 6,273,916 B1 | 8/2001 | Murphy |

OTHER PUBLICATIONS

U.S. patent application Ser. No. 09/828,539, Filed: Apr. 4, 2001; Preissman, Howard, "Enhanced Visibility Materials for Implantation in Hard Tissue".
DePuy Catalogue, 1995, "Mixing Assembly", Cat. No. 5401–33–00; "Cement Injector Gun", Cat. No. 5401–34–000.

Primary Examiner—Cary E. O'Connor
Assistant Examiner—Candice C. Melson
(74) Attorney, Agent, or Firm—McHale & Slavin, P.A.

(57) ABSTRACT

An orthopedic surgical kit for inserting a biological material into the cancellous portion of bone by a minimally invasive technique has several components which are manually operated using a universal handle. The kit includes a docking needle used as a guide for placing a cannula in a bone. The cannula is filled with a biological material, for support or treatment of the bone, and the material is expressed from the cannula by a plunger.

19 Claims, 6 Drawing Sheets

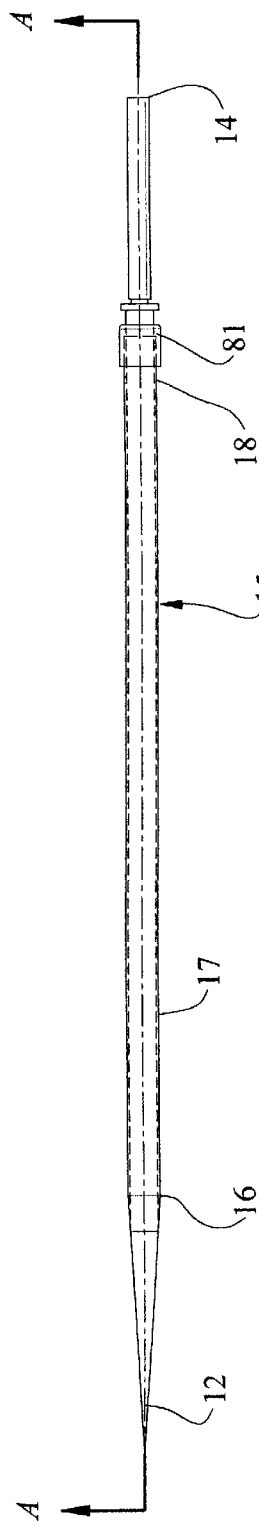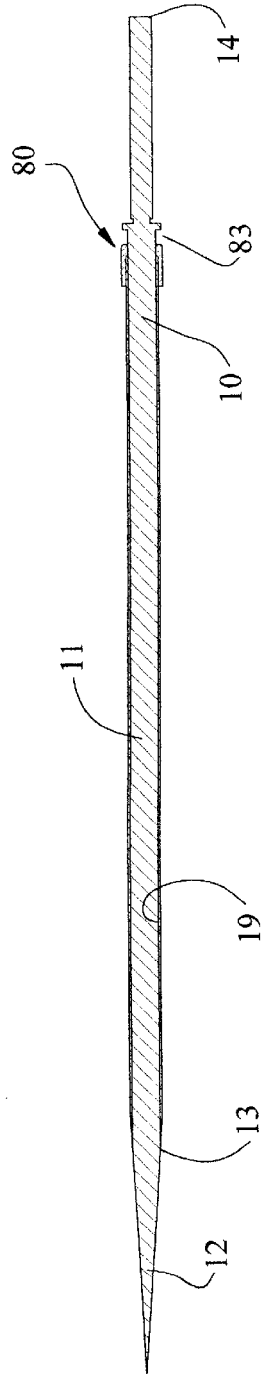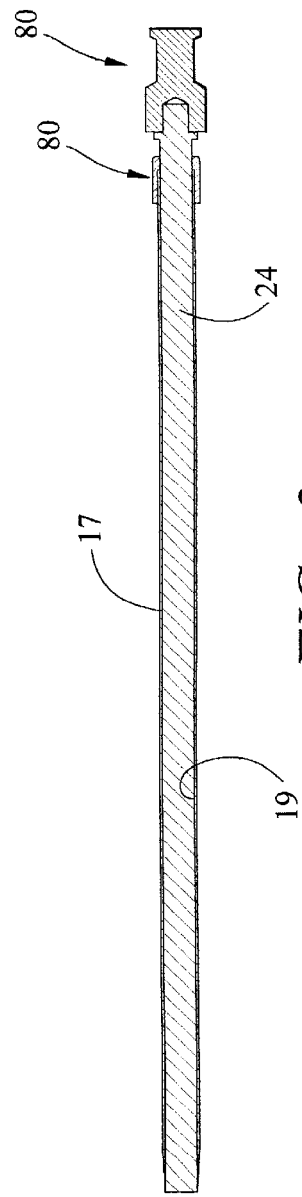

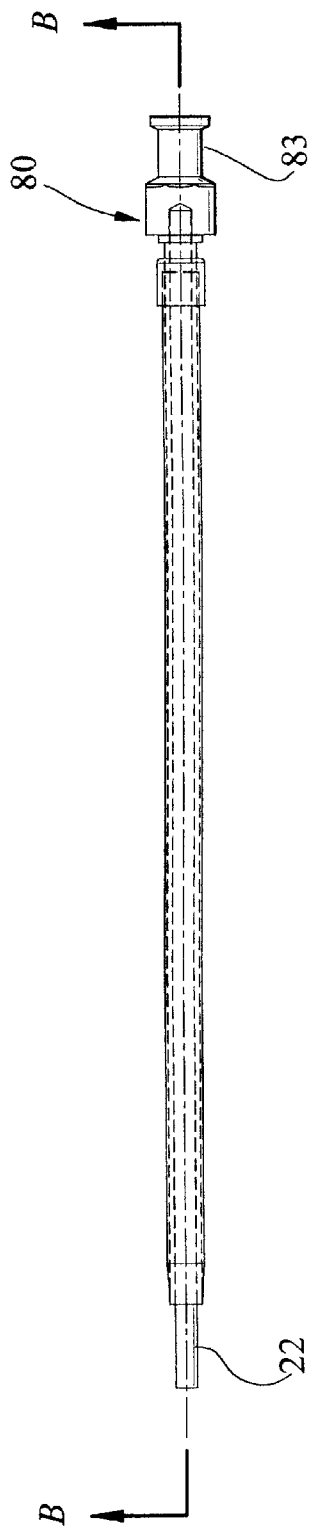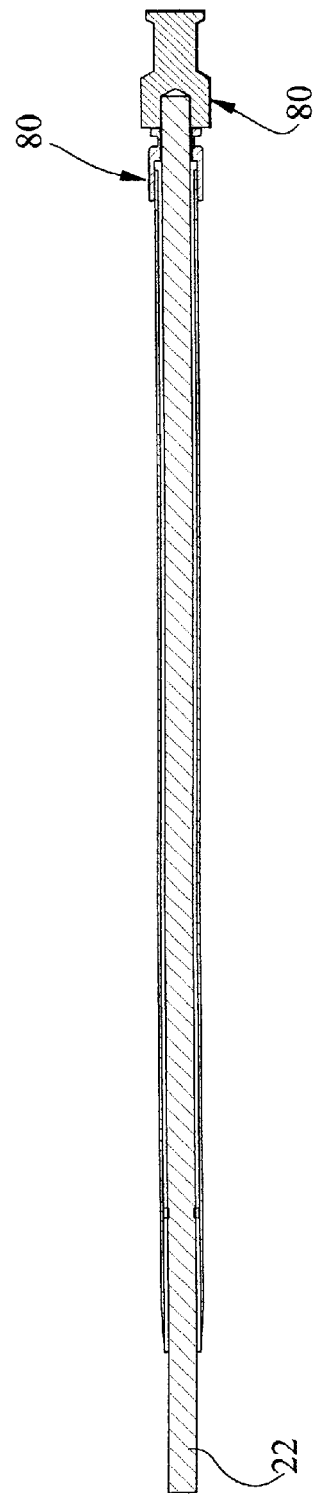
FIG. 4
FIG. 5

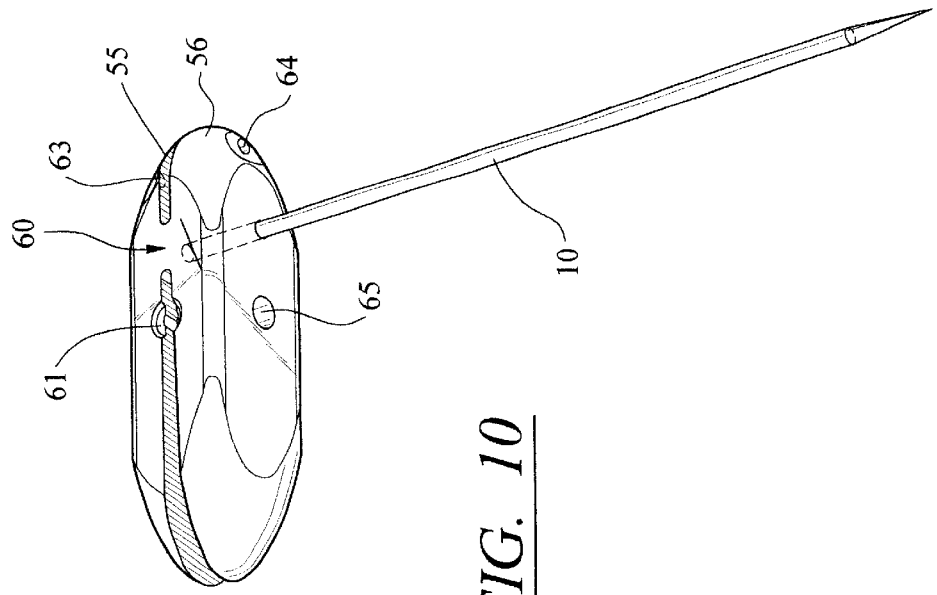
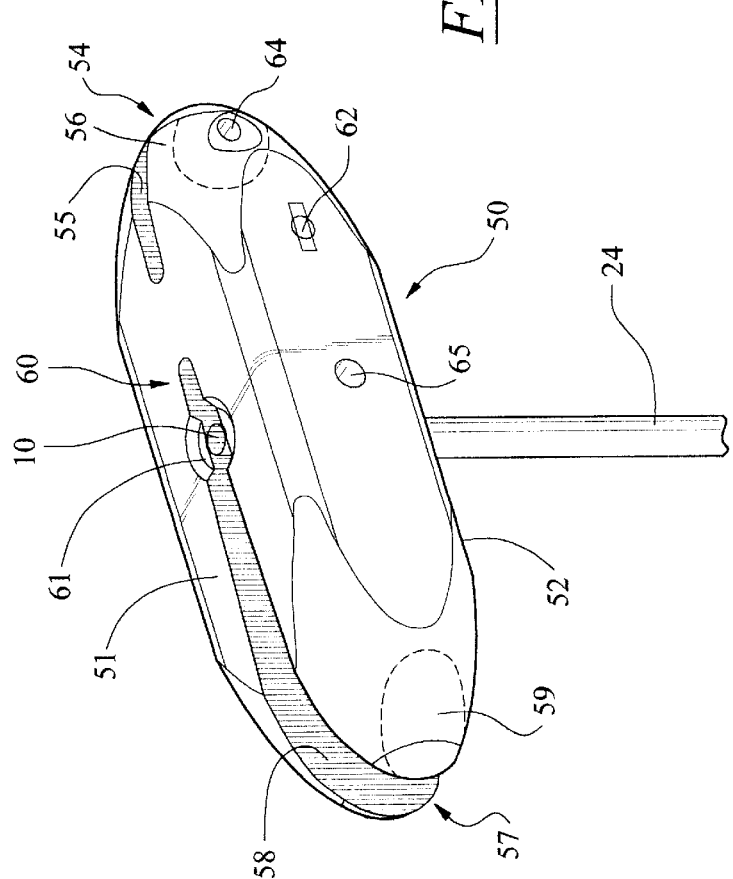
FIG. 9
FIG. 10

VERTEBROPLASTY SYSTEM

FIELD OF THE INVENTION

This invention relates to the orthopedic field of vertebroplasty and to the apparatus and process for injecting biological material into the cancellous portion of bones for treatment and support.

BACKGROUND OF THE INVENTION

Vertebroplasty was introduced to the medical arts as a percutaneous technique for repairing spinal compression fractures by injecting bone cement into the vertebral body. However, the technique quickly expanded to osteoporotic individuals that had been treated with narcotics and immobilization. The bone cement is used to shore up the collapsing vertebrae for support which relieves the pain associated with undue pressure on the nerves.

Radiologists and surgeons are involved in the procedure since the process is monitored by fluoroscopy and has the potential for leakage of the cement into the local blood stream. Some of the critical parameters of the procedure involve the mixing of the cement to an appropriate viscosity, ensuring that the cement is radio-dense for viewing, properly placing the injector inside the cancellous portion of a vertebra, and rigorously controlling injection pressure and quantity. See "Vertebroplasty: Dangerous Learning Curve," START-UP, Jun. 2001.

DESCRIPTION OF THE PRIOR ART

U.S. Pat. No. 6,273,916 to Murphy describes vertebroplasty, generally, as performed on a prepped and draped prone patient who has been injected with a local anaesthetic. A skin incision is made over the selected vertebrae and a needle is inserted in a posterior approach to engage the vertebral body. A suitable cement is prepared using a contrast medium, such as barium powder, mixed with methylmethacrylate powder, and a monomer liquid. The cement (PMMA) becomes unworkable within 4 to 11 minutes from mixing.

Cement is injected into the vertebrae, while visualized by lateral and anterior- posterior X-ray projection fluoroscopy imaging. The injection is halted if the cement starts to extend into unwanted locations, such as the disc space or towards the posterior quarter of the vertebral body where the risk of epidural venous filling and spinal cord compression is greatest. If no unwanted migration is detected, the injection continues until the vertebrae is adequately filled. The amount of cement injected may vary considerably, e.g. from 4 to 36 cc.

Reiley et al, U.S. Pat. No. 6,048,346, teach a posterior-lateral approach for accessing the interior of the vertebrae for injecting bone cement or treatment substances or a combination of both. The bone cement is injected using a caulking gun-like device with a ram rod in the barrel.

Goldenberg et al, U.S. Pat. No. 5,634,473, and Goldenberg, U.S. Pat. No. 5,843,001, both teach a removable handle for biopsy needles used for bone biopsy.

What is needed in the art is a simple apparatus having several components operated by the same handle to perform biopsy and inject high viscosity cement or other biological material or a combination of both in precisely measured quantities.

SUMMARY OF THE INVENTION

Accordingly, it is an objective of the instant invention to teach a kit for biopsy and injection of biological materials having a guide needle, cannulas, several different cannula tips, a plunger, a clearing tool, a connector and a universal tool.

It is a further objective of the instant invention to teach a kit for biopsy and injection of biological materials which is sized to deliver a precise amount of biological material.

It is another objective to teach a kit with several interchangeable tips to be fitted on the leading end of the cannula for different penetrations of the bone.

It is yet another objective of the instant invention to teach a procedure for delivery of a biological material at high viscosity and low pressure.

It is a still further objective of the invention to teach a kit for orthopedic use to perform bone biopsy and to deliver a biological material to the cancellous portion of bone.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 1 is a perspective of the docking needle and a cannula removably telescoped together;

FIG. 2 is a cross section of the telescoped docking needle and cannula taken along line A—A of FIG. 1;

FIG. 3 is a longitudinal cross section of a cannula and a plunger;

FIG. 4 is a perspective of the cannula and clearing tool assembly;

FIG. 5 is a longitudinal cross section of the cannula and clearing tool taken along line B—B of FIG. 4;

FIG. 9 is a perspective of the handle with the needle and plunger engaged;

FIG. 10 is a perspective of the handle with the docking needle engaged;

DETAILED DESCRIPTION OF THE INVENTION

The orthopedic system of this invention is in the form of a kit which includes a docking needle 10 with an elongated shaft 11, shown in FIGS. 1 and 2, having an insertion point 12 for penetration through the cutaneous layer of a patient. The point 12 passes through the skin, muscle and the hard shell of a bone into the softer cancellous bone material. The point 12 forms a tapered end portion with the base of the taper 13 smoothly merging into the shaft 11.

Figure 8:
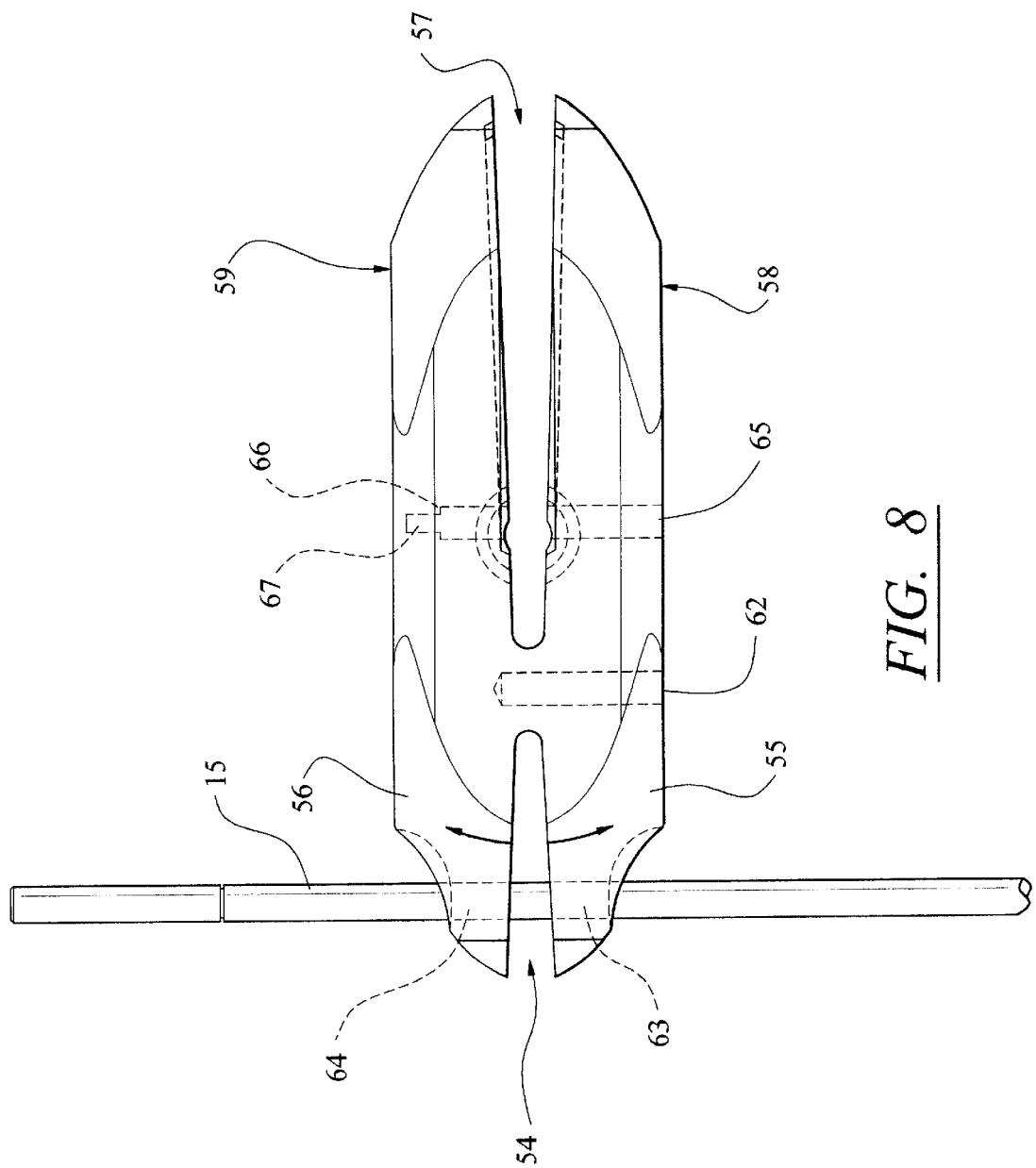
FIG. 8 is a top plan view of the handle with the docking needle engaged.

The needle is of a size and material to withstand the compression required for insertion without deformation. The needle may be made of stainless steel, other metals, or suitable polymers. Normally, the insertion is performed manually by axial pressure at the trailing end 14 of the needle to include striking the needle with a surgical hammer. The tool or handle 50, shown in FIGS. 8, 9, and 10 is designed to fit on the trailing end 14 of the needle for translating the manual axial pressure to the needle 10.

Preferably, in vertebroplasty, the needle 10 is inserted on a posterior-lateral tract, using X-ray fluoroscopy, to dock in a vertebrae anteriorly of the lateral process. Other approaches may be chosen by the surgeon. Regardless, of the orthopedic surgical procedure involved, the docked needle serves as a guide for the subsequent insertion of the cannulas of the system. Of course, in some applications, the needle and cannula may be inserted simultaneously.

In operation, a cannula is telescoped over the docking needle 10 to provide a pathway for removal or delivery of material from the bone. The surgeon removes the handle 50 from the trailing end of the docking needle and connects the handle with the trailing end of the cannula. The leading end of the cannula is then placed over the trailing end of the needle. Axial pressure is applied to the cannula to slide the cannula along the needle to the desired location. Using fluoroscopy, the surgeon telescopes the cannula over the docking needle until the leading end of cannula and the leading end of the docking needle are flush or superimposed within the bone site thereby designating proper placement of the delivery cannula.

FIGS. 1 and 2 show a delivery cannula 15 telescoped over the docking needle. The leading end 16 of the cannula may be tapered to form a smooth transition from the needle point to the cannula shaft 17. In one embodiment, the delivery cannula is included in a kit without an attached leading end. The leading end 16 is selected and placed on the shaft to provide a range of choices to the surgeon. The trailing end 18 of the cannula has a connector 80 either removably affixed by internal threads 82, in the nature of a Leur-type fitting, or permanently connected to the shaft. The connector 80 has external planar surfaces 81 which provide a gripping surface for manipulating the cannula. In one embodiment, the connector has a hex-nut outer surface to prevent rotation within handle 50 although other configurations are a matter of choice. The connector 80 has a reduced diameter portion 83 between a shoulder 84 and a flange 85 to prevent longitudinal movement within the handle 50.

Once the cannula is telescoped over the needle to the desired location within the bone, the handle is removed from the trailing end of the cannula and re-attached to the trailing end of the needle which extends beyond the trailing end of the cannula. Axial force is then applied in the opposite direction to remove the needle from the bone and the cannula. After the needle has been removed, the cannula bore 19 is open for either removing material for biopsy or for dispensing a biological material for treatment.

Figure 6:
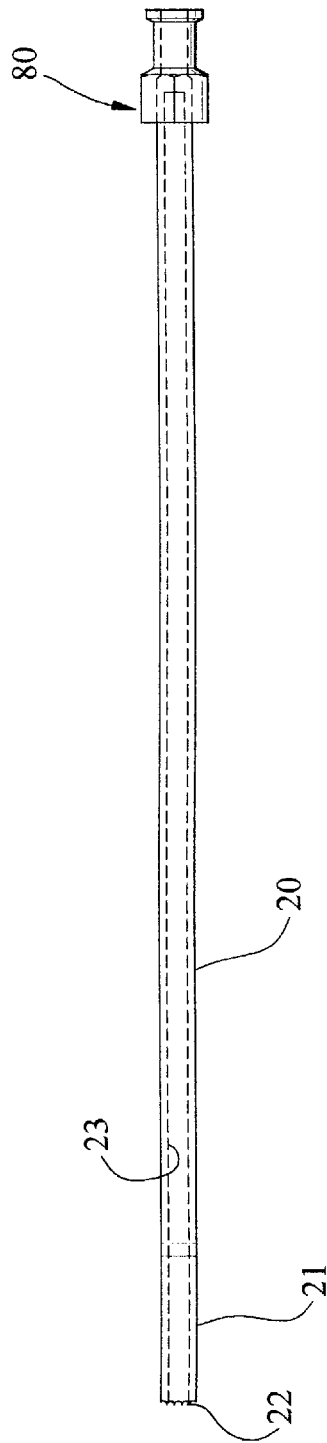
FIG. 6 is a perspective of the biopsy instrument.
Figure 7:
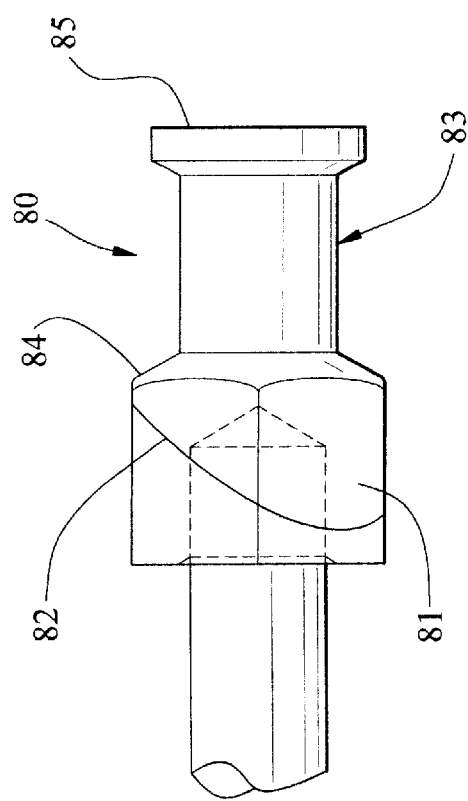
FIG. 7 is a side view of the hex Luer-type fitting.
Figure 11:
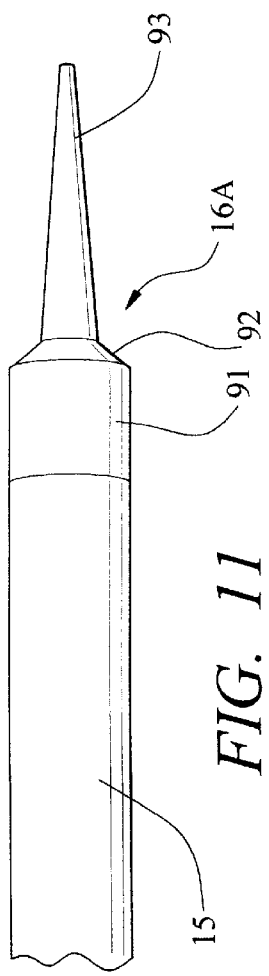
FIG. 11 is a perspective of a modification of the delivery cannula tip.
Figure 12:
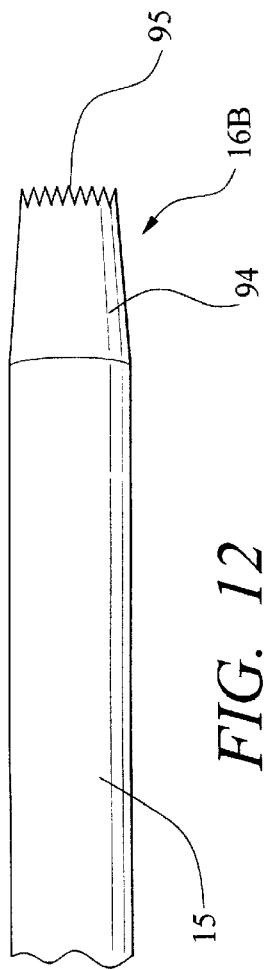
FIG. 12 is a perspective of another modification of the delivery cannula tip.
Figure 13:
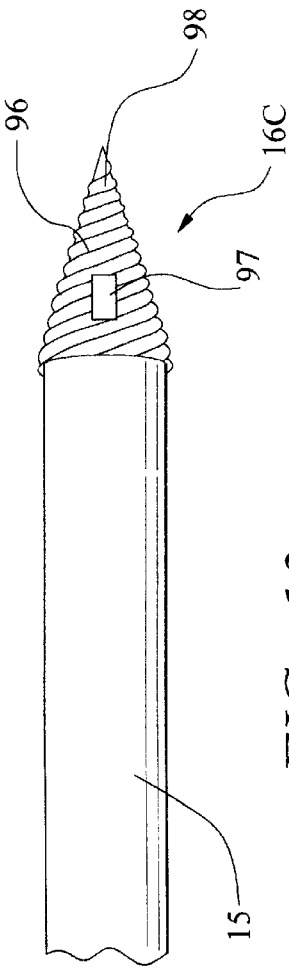
FIG. 13 is a perspective of another modification of the delivery cannula tip.

FIG. 6 shows a biopsy cannula 20 with a leading end having serrations 21. Of course, the leading end 16 of the delivery cannula 15 may be modified to enhance the ability to cut through bone, also, as shown in FIGS. 11–13. Once the biopsy cannula 20 has been manipulated either rotationally or longitudinally or both by the handle 50 engaged with the connector 80, the handle is used to withdraw the cannula from the patient's body. A clearing tool 22, shown in FIGS. 4 and 5, is inserted into the bore 23. The clearing tool 22 is advanced through the bore to push the tissue sample from the cannula.

If a biopsy is not required or after removal of the biopsy cannula, a delivery cannula 15 is telescoped over the docking needle, as described above. The delivery cannula is provided with a connector 80 at its trailing end. The longitudinal dimension of the connector is such that it fits within a recess 61 in the handle 50.

The tool or handle 50, illustrated in FIGS. 8, 9 and 10, is made from surgical stainless steel or other magnetizable or non-magnetizable metals, or, preferably, molded from a high impact polymer, such as polyethylene, polypropylene, NYLON or similar compositions capable of withstanding repeated sterilizations. The handle is flexible and, preferably, resilient. The handle has a top surface 51, a bottom surface 52 and side walls defining a periphery 53. A slit 54 extends through the side walls from the periphery toward the center portion 60. The slit has opposing jaws 55 and 56 which pivot about the center portion. The jaws 55 and 56 each have a bore 63 and 64, respectively, oriented in the same plane in which each jaw pivots.

Another slit 57 extends through the side walls from the periphery toward the center portion. Slit 57 has opposing jaws 58 and 59 which pivot about the center portion 60. The jaws 58 and 59 each have a flange for engaging the reduced diameter portion of the connector 80.

By applying pressure on the opposing pairs of jaws of each slit, the jaws may approach with each other. When pressure is released, the respective pairs of jaws resiliently move away from each other. As illustrated, the slits are arranged to oppose each other.

A blind bore 62 is formed in the periphery of the handle for the purpose of engaging the trailing end of the docking needle. The shaft of the blind bore 62 is shaped to cooperate with the trailing end of the needle to provide rotation of the needle upon rotation of the handle. The surgeon manually grips the handle and applies longitudinal and/or rotational force through the handle to the needle to penetrate the soft tissue and bone of the patient. The handle may also provide a striking plate for receiving blows from a surgical hammer for driving the needle into the bone. Once the needle is properly docked in the bone, the handle is removed from the needle.

Blind bore 65 is of suitable size to accommodate the trailing end of the cannula fitted with a connector 80. As shown in FIG. 8, the blind bore 65 has a larger diameter terminating with a shoulder 66 which will engage and stop the connector 80. A smaller diameter portion 67 of the bore continues above the shoulder to allow the trailing end of the docking needle to extend beyond the trailing end of the connector 80. Because the cannula is somewhat larger than the docking needle, the tip of the cannula may be sharpened to cut through the bone. A surgical hammer may be used to drive the delivery cannula, at least, through the hard outer shell of the bone. Once the cannula is located in the cancellous portion of the bone, the cannula may be removed from the blind bore 65.

The cannula with an attached connector 80 may then placed in the slit 57, of the handle, with the connector 80 in recess 61. The connector 80 is engaged with the jaws 58 and 59 to prevent longitudinal or rotational movement of the cannula within the handle. The surgeon telescopes the leading end of the cannula over the trailing end of the needle and again applies longitudinal force through the handle to the cannula to force the cannula through soft tissue and into the bone. As the cannula approaches the proper position in the bone, the trailing end 14 of the telescoped docking needle emerges from the trailing end of the cannula. When the trailing end of the needle 14 is level with the top surface 51 of the handle, the leading end 16 of the cannula is flush with the end of the needle. The top surface 51 of the handle and the trailing end 14 of the needle serve as a visual and tactile gauge, in the surgeon's hand, for properly placing the leading end of the cannula in the bone.

The handle 50 is then removed from the cannula and the jaws of slit 54 are pivoted to place the bores 63 and 64 in parallel. The trailing end of the needle is then inserted through bores 63 and 64. The pivoting pressure on jaws 55 and 56 is then released causing the bores to resiliently intersect engaging the shaft of the needle, as shown in FIG. 8. Of course, the tool 50 may operate in reverse, with the pivoting pressure causing the jaws to close, in another embodiment. The needle is then removed from the cannula by use of the handle 50. After the needle is removed from the cannula the jaws are pivoted to release the shaft of the needle and free the handle.

In FIGS. 11, 12, and 13, alternate removable tips 16A, 16B and 16C are shown. The kit may be supplied with several interchangeable tips to provide the surgeon with flexibility in dealing with anomalies of the bones or individual preference. Also, if a larger diameter delivery cannula is needed for the proper amount of biological substance, a relatively smaller tip can be used to penetrate the bone. In FIG. 11, the delivery cannula 15 has a removable tip 91 with a necked down portion 92 and a smaller leading end portion 93 that penetrates the hard outer shell of the bone.

FIG. 12 shows another tip 16B that is tapered to a leading end 94 with serrations 95 which may be necessary to cut through the dense bone.

FIG. 13 illustrates another tip 16C which has a tapered leading end and a closed point 98. The tapered tip has screw threads 96 for auguring into bone. The delivery port 97 is on the lateral aspect of the leading end.

Other replaceable tips 16 may have other shapes or a variety of cannulas may be furnished with permanent tips.

The delivery cannula is now positioned to transmit the biological material to the bone. In general, the biological substance may be either structural or a treating agent or a combination of both.

For example, the material may be selected from such groups of substances as BMP, bone morphogenic proteins, DBM, demineralized bone matrix, BOTOX and other viral vectors, any bone marrow aspirate, platelet rich plasma, composite ceramic hydroxyapatite, tricalcium phosphate, glass resin mixtures, resorbable highly purified polylacttides/polylactides-co-glycolides and others. The treating agent may include hormonal, antibiotic, anti-cancer, or growth factor substances, among others. In vertebroplasty, polymethylmethacrylate (PMMA) is the customary bone cement though other compounds may be used.

Regardless of the chemical make-up of the biological substance, this system preferably uses a high viscosity biological material delivered through the cannula at a low pressure. To accomplish this objective, after the delivery cannula is properly placed in the bone, it is filled with a biological material having a viscosity allowing it to flow into the cannula. The viscosity of some of the materials continues to increase within the cannula to reach a consistency acceptable to the surgeon. Other materials may be ready for use, when loaded in the cannula.

When the material is sufficiently stiff, the surgeon inserts a plunger 24 into the cannula 15 to express the biological substance into the cancellous portion of the bone. The plunger 24 is fitted with a connector 80 and manipulated by handle 50. As shown in FIG. 3, both the plunger 24 and the cannula 15 are telescoped together and the plunger is sized to substantially co-terminate with the leading end of the delivery cannula when both the connectors 80 are in contact. The diameter of the plunger is slightly less than the diameter of the cannula to provide a vent for the system. The viscosity of the biological material will be such that the entire amount of the material will be expressed from the cannula. In this instance, the amount of biological material delivered is precisely measured to be the corresponding volume of the delivery cannula, for example, 4 cc.

Of course, the amount of biological material may be adjusted to a particular patient. This is accomplished through the continued fluoroscopic observance of the procedure. If more material is necessary in a particular procedure, the syringe used to load the delivery cannula may be utilized to pre-load the bone cavity before the plunger is inserted into the delivery cannula.

When the appropriate amount of biological material has been injected into the bone, the handle 50 is used to rotate and withdraw the plunger 24. Once the biological substance has begun to solidify, the handle is placed on the delivery cannula and twisted to rotate the cannula thereby separating the cannula from the substance. The cannula is subsequently withdrawn from the bone.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A surgical kit for orthopedic procedures comprising a docking needle for penetration of the soft tissue of the body and lodgement in a bone, a cannula having a sharpened leading end, a trailing end for carrying a connector, and a bore of sufficient size to telescope over said needle, a plurality of connectors, and a tool for sequential manipulation of said needle and said cannula, said tool having a center portion and a periphery, a first slit in said tool between said periphery and said center portion, said first slit having a first jaw and a second jaw opposed to said first jaw, said first and second jaws pivoting about said center portion, said first jaw having a first bore therethrough, said second jaw having a bore therethrough, said first bore and said second bore being aligned when said first and second jaws are closed, said first and second bores intersecting when said first and second jaws are open whereby said docking needle may pass through said aligned bores and be frictionally bound by said intersecting bores to grip said needle for removal.

2. A surgical kit of claim 1 wherein said tool has a blind bore extending partially therethrough, said blind bore having a diameter approximating the diameter of said needle, whereby said tool protects an end of said needle and provides a means for applying force to said needle to penetrate through the cutaneous layer and dock said needle in a bone.

3. A surgical kit of claim 2 wherein said docking needle has a trailing end with shaped sidewalls and said blind bore has sidewalls of corresponding shape whereby said needle can be rotated by said handle.

4. A surgical kit of claim 2 wherein said kit comprises a clearing tool for said cannula, said clearing tool having a leading end and a trailing end, said leading end being closed, said clearing tool sized to telescope through said cannula for removing any soft tissue and bone from said cannula.

5. A surgical kit of claim 2 wherein a second slit is formed in said tool between said periphery and said center portion, said second slit having a third jaw opposed to a fourth jaw, said third and fourth jaws pivoting about said center portion, said third and fourth jaws cooperating with said cannula whereby said cannula may be manipulated by said handle to telescope over said needle for penetration into the bone and for removal therefrom.

6. A surgical kit of claim 5 wherein said third and fourth jaws have a receiver adapted to accommodate said connector on said cannula.

7. A surgical kit of claim 5 wherein said first slit and said second slit are opposed to each other.

8. A surgical kit of claim 7 wherein said tool is made of a high impact polymer and said first and second slits pivot resiliently about said center portion.

9. A surgical kit of claim 1 wherein said kit comprises a delivery cannula and a plunger, said delivery cannula having a leading end and a trailing end, a connector on said trailing end, said delivery cannula sized to telescope over said docking needle, said tool adapted to cooperate with said connector for proper placement of said cannula in a bone, said delivery cannula adapted to deliver a measured amount of a biological substance to the bone, said plunger sized to telescope through said delivery cannula for expressing a biological substance from within said delivery cannula.

10. A surgical kit of claim 9 wherein said kit comprises a clearing tool for said cannula, said clearing tool having a leading end and a trailing end, said leading end being closed, said clearing tool sized to telescope through said cannula for removing any soft tissue and bone from said cannula.

11. A surgical kit of claim 9 wherein said kit comprises a quantity of biological substance, said biological substance being one of the group consisting of bone cement, growth factor, hormonal composition, blood component, or graft material, said biological substance having an initial viscosity adapted for placement in said delivery cannula.

12. A surgical kit of claim 11 wherein said biological substance has a second higher viscosity whereby substantially all of said biological substance is expressed by the telescopic movement of said plunger.

13. A surgical kit for delivering a biological substance within the cancellous portion of a bone comprising a docking needle having a sharp end and a trailing end, a delivery cannula having a leading end, a bore sized to telescope over said needle and a trailing end with a connector, a plunger having a smaller diameter than said bore and a length to extend through said cannula to said leading end for delivery of a biological substance, and a handle for sequentially manipulating said docking needle, said delivery cannula, and said plunger, said handle having a center portion and a periphery, at least one slit in said handle between said periphery and said center portion, said slit having opposite surfaces, said opposite surfaces defining a receiver for said connector, said receiver preventing rotation of said cannula in said handle.

14. A surgical kit of claim 13 wherein said handle has a gauge adapted to indicate location of said leading end of said delivery cannula, said handle having a top surface and a bottom surface, said delivery cannula adapted to protrude from said bottom surface when said connector is in said receiver, said top surface of said slit having a recess, said connector of said delivery cannula disposed in said recess, the length of said docking needle, said delivery cannula, and the depth of said recess inter-related whereby said trailing end of said docking needle and said top surface are substantially co-planar when said delivery cannula has been telescoped a proper distance.

15. A surgical kit of claim 13 wherein said handle has a blind bore sized to accept said trailing end of said docking needle for securing said needle and transmitting force whereby said needle penetrates the bone.

16. A surgical kit of claim 13 wherein said handle is made of high impact polymer and said opposite surfaces of said slit resiliently pivot about said center portion.

17. A surgical kit of claim 13 wherein said leading end of said delivery cannula is removable and said kit includes a multiplicity of interchangeable leading ends having different shapes.

18. A surgical kit of claim 13 wherein said handle has a blind bore sized to accommodate said delivery cannula and said connector.

19. A surgical kit of claim 18 wherein said handle has a blind bore sized to accept said trailing end of said docking needle.

* * * * *